United States Patent
Babu et al.

(10) Patent No.: US 12,156,971 B2
(45) Date of Patent: Dec. 3, 2024

(54) INDWELLING URINARY CATHETER WITH GUIDEWIRE ANCHORING MECHANISM

(71) Applicant: C. R. Bard, Inc., Franklin Lakes, NJ (US)

(72) Inventors: M. P. Dinesh Babu, Chennai (IN); Bharath Kumar Vishnuraj, Kanchipuram (IN)

(73) Assignee: C. R. Bard, Inc., Franklin Lakes, NJ (US)

( * ) Notice: Subject to any disclaimer, the term of this patent is extended or adjusted under 35 U.S.C. 154(b) by 196 days.

(21) Appl. No.: 17/701,347

(22) Filed: Mar. 22, 2022

(65) Prior Publication Data

US 2022/0305232 A1    Sep. 29, 2022

Related U.S. Application Data

(60) Provisional application No. 63/164,939, filed on Mar. 23, 2021.

(51) Int. Cl.
*A61M 25/00* (2006.01)
*A61M 25/02* (2006.01)
*A61M 25/09* (2006.01)

(52) U.S. Cl.
CPC ........ *A61M 25/0017* (2013.01); *A61M 25/02* (2013.01); *A61M 25/09* (2013.01);
(Continued)

(58) Field of Classification Search
CPC .. A61M 25/0017; A61M 25/02; A61M 25/09; A61M 2025/0293;
(Continued)

(56) References Cited

U.S. PATENT DOCUMENTS 2,616,429 A * 11/1952 Merenlender ......... A61M 25/04
604/105
2,649,092 A *  8/1953 Wallace ............... A61M 25/04
604/105

(Continued)

FOREIGN PATENT DOCUMENTS

DE         4115007 A1 * 11/1992
GB          688450 A      3/1953
(Continued)

OTHER PUBLICATIONS

PCT/US2022/017734 filed Feb. 24, 2022, International Search Report and Written Opinion dated Jan. 4, 2023.

*Primary Examiner* — Adam Marcetich
(74) *Attorney, Agent, or Firm* — Rutan & Tucker LLP

(57) ABSTRACT

Disclosed herein is an indwelling urinary catheter having a guidewire anchoring mechanism. The indwelling urinary catheter includes a catheter tube having a proximal opening, a distal opening, a catheter tube lumen with the catheter tube having a first wall thickness. The guidewire anchoring mechanism is configured to transition between an insertion state and an anchored state. The guidewire anchoring mechanism can include a proximal portion having a top cap, a collapsible section having a second wall thickness less than the first wall thickness, and a distal portion including a holder cap coupled to a holder. The holder can be coupled to the catheter tube, the distal portion can be in communication with the proximal portion, and a guidewire can be coupled to the proximal portion, the guidewire extending through the catheter tube lumen to the distal portion.

19 Claims, 7 Drawing Sheets

(52) U.S. Cl.
CPC .............. *A61M 2025/0293* (2013.01); *A61M 2025/09125* (2013.01)

(58) Field of Classification Search
CPC ........ A61M 2025/09125; A61M 27/00; A61M 25/04; A61M 2210/1085; A61M 25/0074; A61M 25/01; A61M 2025/0163; A61M 25/0147
See application file for complete search history.

(56) References Cited

U.S. PATENT DOCUMENTS

| | | | |
|---|---|---|---|
| 3,108,595 A | | 10/1963 | Overment |
| 3,799,172 A | * | 3/1974 | Szpur .................... A61M 25/04 604/105 |
| 3,938,530 A | * | 2/1976 | Santomieri ........... A61M 25/04 604/105 |
| 4,228,802 A | * | 10/1980 | Trott .................... A61M 25/00 604/105 |
| 4,973,329 A | * | 11/1990 | Park .................. A61B 17/3403 606/1 |
| 4,995,868 A | | 2/1991 | Brazier |
| 5,352,198 A | | 10/1994 | Goldenberg et al. |
| 5,441,483 A | * | 8/1995 | Avitall ............... A61B 18/1492 604/95.05 |
| 5,522,400 A | | 6/1996 | Williams |
| 6,508,789 B1 | | 1/2003 | Sinnott et al. |
| 8,114,073 B2 | | 2/2012 | Whayne et al. |
| 8,496,644 B2 | | 7/2013 | Graffam et al. |
| 8,734,426 B2 | | 5/2014 | Ahmed et al. |
| 9,950,138 B2 | | 4/2018 | O'Callaghan et al. |
| 2002/0177869 A1 | * | 11/2002 | Eidenschink ... A61M 25/09041 606/194 |
| 2003/0233043 A1 | * | 12/2003 | Windheuser ...... A61M 25/0172 600/434 |
| 2004/0030290 A1 | * | 2/2004 | Mangano ............... A61M 25/01 604/164.04 |
| 2004/0243104 A1 | | 12/2004 | Seddon |
| 2005/0101941 A1 | * | 5/2005 | Hakky .............. A61M 25/0017 604/544 |
| 2005/0245900 A1 | | 11/2005 | Ash |
| 2006/0229553 A1 | | 10/2006 | Hammack et al. |
| 2007/0135762 A1 | * | 6/2007 | Scopton ........... A61M 16/0493 604/77 |
| 2008/0194913 A1 | * | 8/2008 | Tinkham ................ A61B 1/018 600/154 |
| 2009/0318873 A1 | | 12/2009 | Bailey |
| 2010/0174139 A1 | * | 7/2010 | Windheuser .... A61M 25/09041 604/528 |
| 2015/0196730 A1 | | 7/2015 | O'Callaghan et al. |
| 2019/0009053 A1 | | 1/2019 | Adams et al. |
| 2020/0360667 A1 | * | 11/2020 | Aklog ................... A61M 39/10 |
| 2021/0196926 A1 | | 7/2021 | Malinaric et al. |

FOREIGN PATENT DOCUMENTS

| | | | | |
|---|---|---|---|---|
| KR | 20180041437 A | * | 4/2018 | ........ A61M 25/0136 |
| WO | 2021224248 A1 | | 11/2021 | |
| WO | WO-2022153064 A1 | * | 7/2022 | ........... A61F 2/0018 |
| WO | 2023163704 A1 | | 8/2023 | |

\* cited by examiner

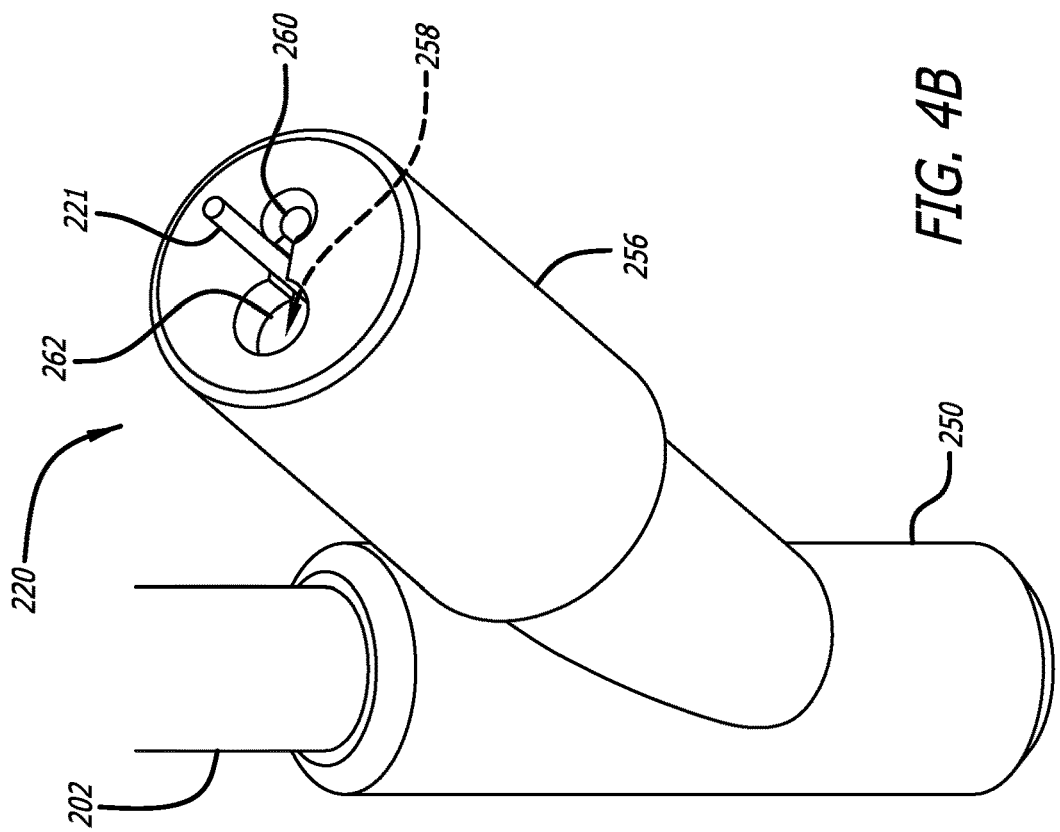
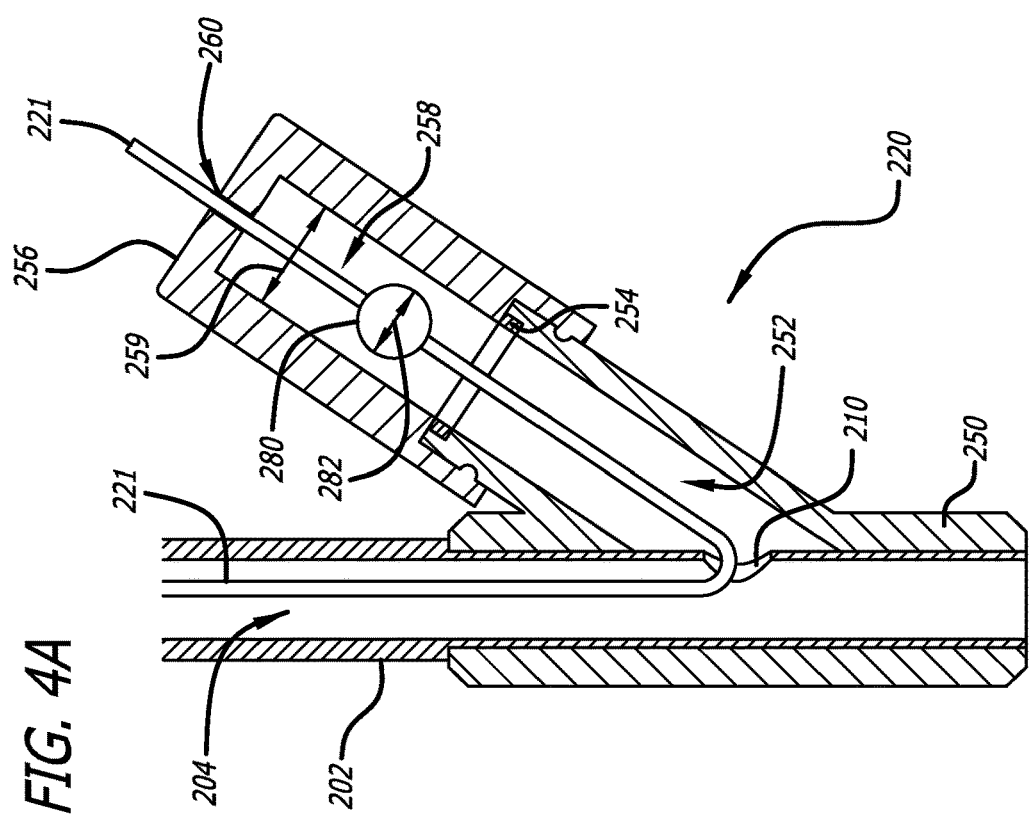
FIG. 4A
FIG. 4B

INDWELLING URINARY CATHETER WITH GUIDEWIRE ANCHORING MECHANISM

PRIORITY

This application claims the benefit of priority to U.S. Provisional Application 63/164,939, filed Mar. 23, 2021, which is incorporated by reference in its entirety into this application.

BACKGROUND

Many indwelling urinary catheter devices use a balloon to anchor the catheter within the bladder. However, the balloon can fail to deflate, causing extreme pain during removal. Deflating the balloon can be a complicated process involving a clinician attempting to chemically dissolve the balloon possibly irritating the patient, or attempting to puncture the balloon, possibly leading to bladder injury. It would be beneficial to the patient and the clinician to have an indwelling catheter that avoids the risk of balloon failure. Disclosed herein is an apparatus and method of use that address the foregoing.

SUMMARY

Disclosed herein is an indwelling urinary catheter having a guidewire anchoring mechanism. The indwelling urinary catheter includes a catheter tube having a proximal opening, a distal opening, a catheter tube lumen with the catheter tube having a first wall thickness. The guidewire anchoring mechanism is configured to transition between an insertion state and an anchored state. The guidewire anchoring mechanism includes a proximal portion including a top cap and a collapsible section having a second wall thickness less than the first wall thickness, a distal portion including a holder cap coupled to a holder, where the holder is coupled to the catheter tube, the distal portion being in communication with the proximal portion, and a guidewire coupled to the proximal portion and extending through the catheter tube lumen to the distal portion.

In some embodiments, a distal end of the guidewire includes a guidewire bump.

In some embodiments, the collapsible section includes a plurality of vertical slits that define a plurality of flexible bands, the plurality of flexible bands being configured to exist in a vertical position or be horizontally extended.

In some embodiments, the top cap is coupled to the proximal opening of the catheter tube, and a top cap ring distally extends from the top cap into the catheter tube lumen.

In some embodiments, the distal portion includes the holder having a holder lumen configured to receive the distal end of the guidewire, and the holder cap having a holder cap channel in communication with each of a first guidewire channel and a second guidewire channel, each of the first guidewire channel and second guidewire channel configured to receive the distal end of the guidewire.

In some embodiments, the catheter tube lumen includes a guidewire opening configured to allow the guidewire to be threaded from the catheter tube lumen to the holder.

In some embodiments, the second guidewire channel is configured to receive the guidewire bump, and the first guidewire channel is configured to receive only the distal end of the guidewire.

In some embodiments, the holder lumen is separated from the holder cap channel by a septum configured to provide a fluid tight seal preventing fluid traveling through the catheter tube lumen to reach the holder cap.

In some embodiments, a proximal end of the guidewire is threaded through the top cap ring and coupled to the guidewire.

In some embodiments, the proximal end of the guidewire is threaded through the top cap ring and coupled to the guidewire by a crimp bead.

In some embodiments, the insertion state includes the distal end of the guidewire extending through the first guidewire channel and the plurality of flexible bands being in a vertical position.

In some embodiments, the anchored state includes the plurality of flexible bands being horizontally extended and the guidewire bump being pulled through the second guidewire channel.

In some embodiments, a pulling force on the distal end of the guidewire transitions the guidewire anchoring mechanism from the insertion state to the anchored state.

In some embodiments, the indwelling urinary catheter is biased to the insertion state.

Also disclosed herein is a method of anchoring an indwelling urinary catheter in a bladder. The method includes configuring an indwelling urinary catheter for insertion into the bladder, the indwelling urinary catheter having a guidewire anchoring mechanism configured in an insertion state, inserting the indwelling urinary catheter into the bladder, transitioning the guidewire anchoring mechanism to an anchored state, and anchoring the indwelling urinary catheter within the bladder.

In some embodiments, configuring an indwelling urinary catheter for insertion into the bladder includes the indwelling urinary catheter having a catheter tube including a proximal opening, a distal opening, a catheter tube lumen, the catheter tube having a first wall thickness, and the guidewire anchoring mechanism having a collapsible section having a second wall thickness less than the first wall thickness, the collapsible section configured in the insertion state, where the collapsible section includes a plurality of vertical slits that define a plurality of flexible bands, the plurality of flexible bands in a vertical orientation and a distal end of a guidewire extending through a first guidewire channel of a holder cap.

In some embodiments, transitioning the guidewire anchoring mechanism to an anchored state includes transitioning the collapsible section to the anchored state, where the plurality of flexible bands are horizontally extended and a guidewire bump of the distal end of the guidewire is pulled through a second guidewire channel of the holder cap.

In some embodiments, transitioning the guidewire anchoring mechanism to an anchored state includes a pulling force on the distal end of a guidewire transitioning the collapsible section to the anchored state.

In some embodiments, a pulling force on the distal end of the guidewire transitioning the collapsible section to the anchored state includes a proximal end of the guidewire threaded through a top cap ring of a top cap coupled to a proximal opening of the catheter tube, the pulling force collapsing the collapsible section to horizontally extend the plurality of flexible bands.

In some embodiments, anchoring the indwelling urinary catheter within the bladder including maintaining the guidewire anchoring mechanism in the anchored state within the bladder by transitioning the distal end of the guidewire to the first guidewire channel.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4A illustrates a cross-sectional view of a distal portion of the guidewire anchoring mechanism, in accordance with some embodiments.

FIG. 4B illustrates a perspective view of the distal portion of the guidewire anchoring mechanism, in accordance with some embodiments.

DESCRIPTION

Figure 1:
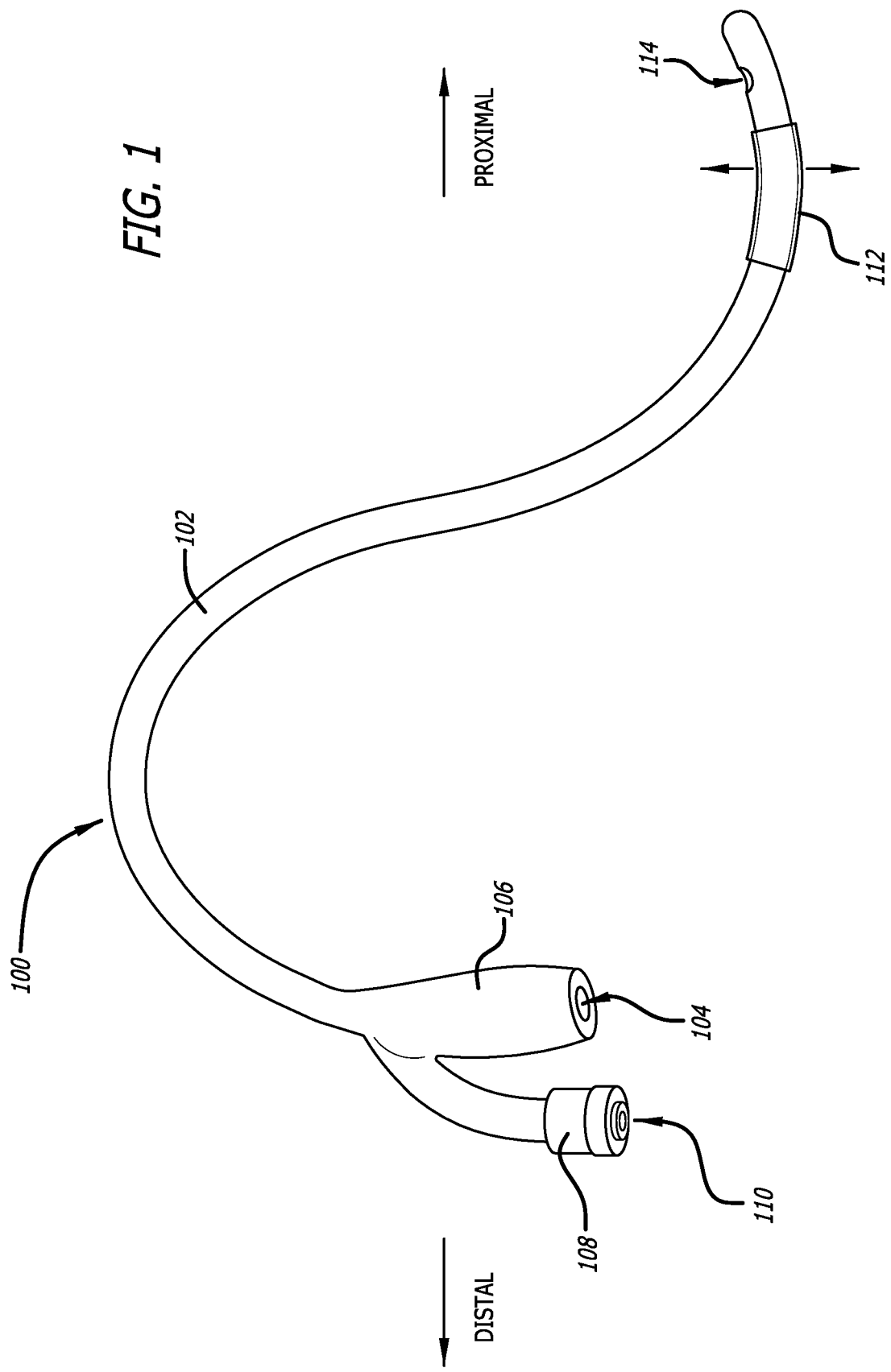
FIG. 1 illustrates a perspective view of an indwelling catheter, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

FIG. 1 illustrates a perspective view of an indwelling urinary catheter 100. The indwelling urinary catheter 100 includes a catheter tube 102 having a proximal end, a distal end, and a catheter tube lumen 104 therethrough. The catheter tube 102 including the proximal end is configured to be inserted into a bladder of a patient. The distal end includes an urine drainage port 106 configured to drain fluid from the bladder, and a balloon port 108 including a balloon port lumen 110 in fluid communication with a balloon 112 coupled to the proximal end of the catheter tube 102. The proximal end includes a bladder opening 114 in fluid communication with the catheter tube lumen 104. Fluid from the bladder may enter the bladder opening 114, move through the catheter tube lumen 104, and exit the indwelling urinary catheter 100 through the urine drainage port 106. To anchor the indwelling urinary catheter 100 within the bladder, the balloon 112 may expand outward as the balloon 112 is inflated with a fluid through the balloon port 108. When the indwelling urinary catheter 100 needs to be removed from the bladder, the balloon 112 must be deflated. However, if there is a blockage in the balloon port lumen 110, the balloon 112 will not deflate leading to pain and discomfort of the patient during removal of the indwelling urinary catheter 100.

Figure 2:
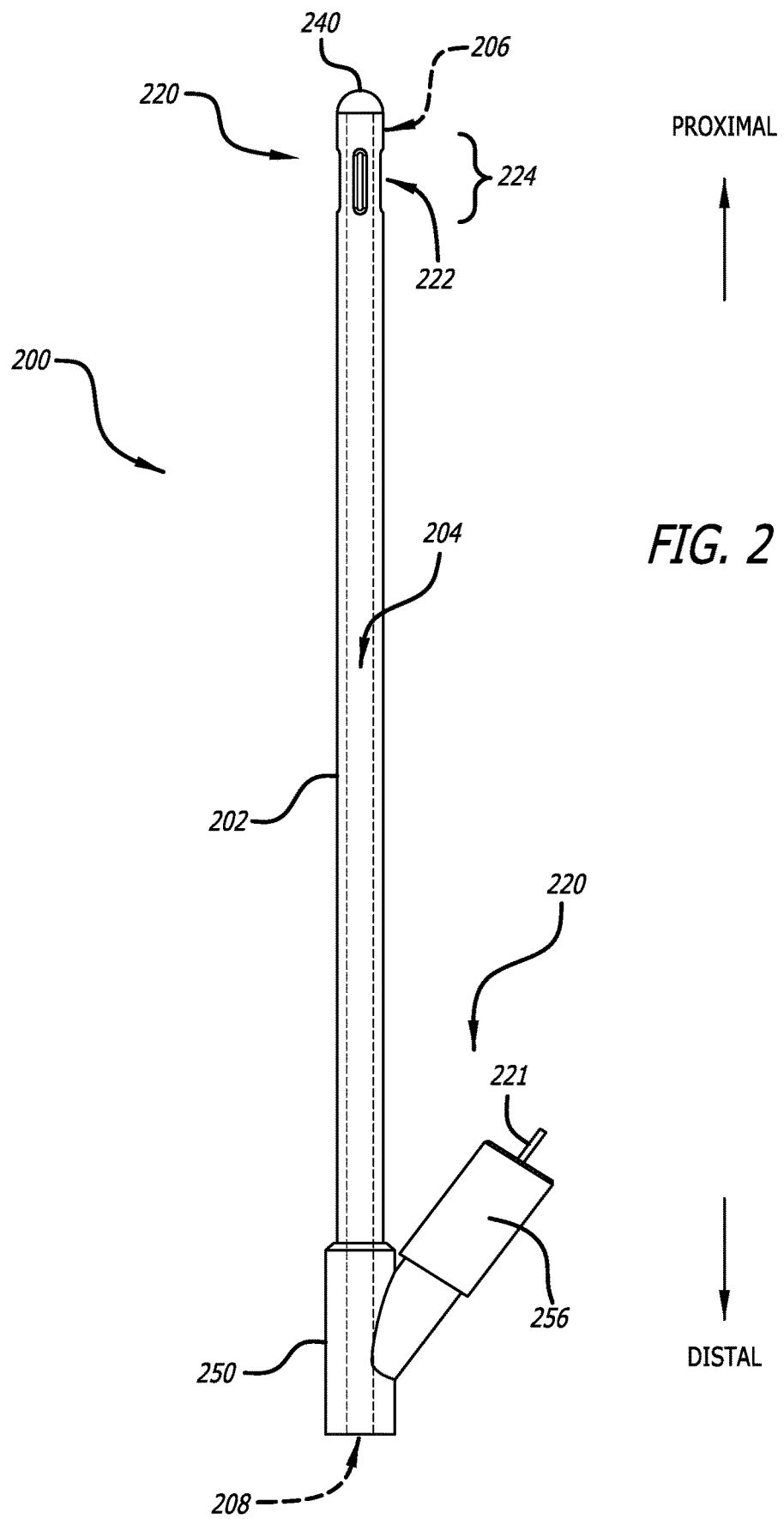
FIG. 2 illustrates a side perspective view of the indwelling catheter including an guidewire anchoring mechanism, in accordance with some embodiments.

FIG. 2 illustrates a side perspective view of an indwelling urinary catheter 200 ("catheter") including a guidewire anchoring mechanism 220, in accordance with some embodiments. In some embodiments, the indwelling urinary catheter 200 includes a catheter tube 202 having a proximal end that includes a proximal opening 206 and a distal end that includes a distal opening 208. The catheter tube 202 includes a catheter tube lumen 204 extending from the proximal opening 206 to the distal opening 208. The catheter 200 includes the guidewire anchoring mechanism 220 having a proximal portion and a distal portion. The proximal portion of the guidewire anchoring mechanism 220 is at the proximal end of the catheter tube 202 and the distal portion of the guidewire anchoring mechanism 220 is at the distal end of the catheter tube 202.

In some embodiments, the proximal portion of the guidewire anchoring mechanism 220 including a top cap 240 and a collapsible section 224 including a bladder opening 222, that will be described in more detail herein. In some embodiments, the distal portion of the guidewire anchoring mechanism 220 including a holder 250 having a holder cap 256, the holder 250 being coupled to the catheter tube 202. The proximal portion of the guidewire anchoring mechanism 220 is in communication with the distal portion of the guidewire anchoring mechanism 220. In some embodiments, a guidewire 221 may be coupled to the proximal portion of the guidewire anchoring mechanism 220 and threaded through the catheter tube lumen 204 to the distal portion of the guidewire anchoring mechanism 220. In some embodiments, the catheter tube lumen 204 is in fluid communication with the bladder opening 222 and the distal opening 208 of the catheter tube 202, allowing fluid to travel from the bladder into the bladder opening 222, through the catheter tube lumen 204, and out of the distal opening 208. The guidewire anchoring mechanism 220 uses mechanical movement of the guidewire anchoring mechanism 220 to anchor the catheter 200 in the bladder. Advantageously, the catheter 200 having the guidewire anchoring mechanism 220 allows the catheter 200 to easily transition between an insertion state and an anchored state, that will be described in more detail herein.

Figure 3B:
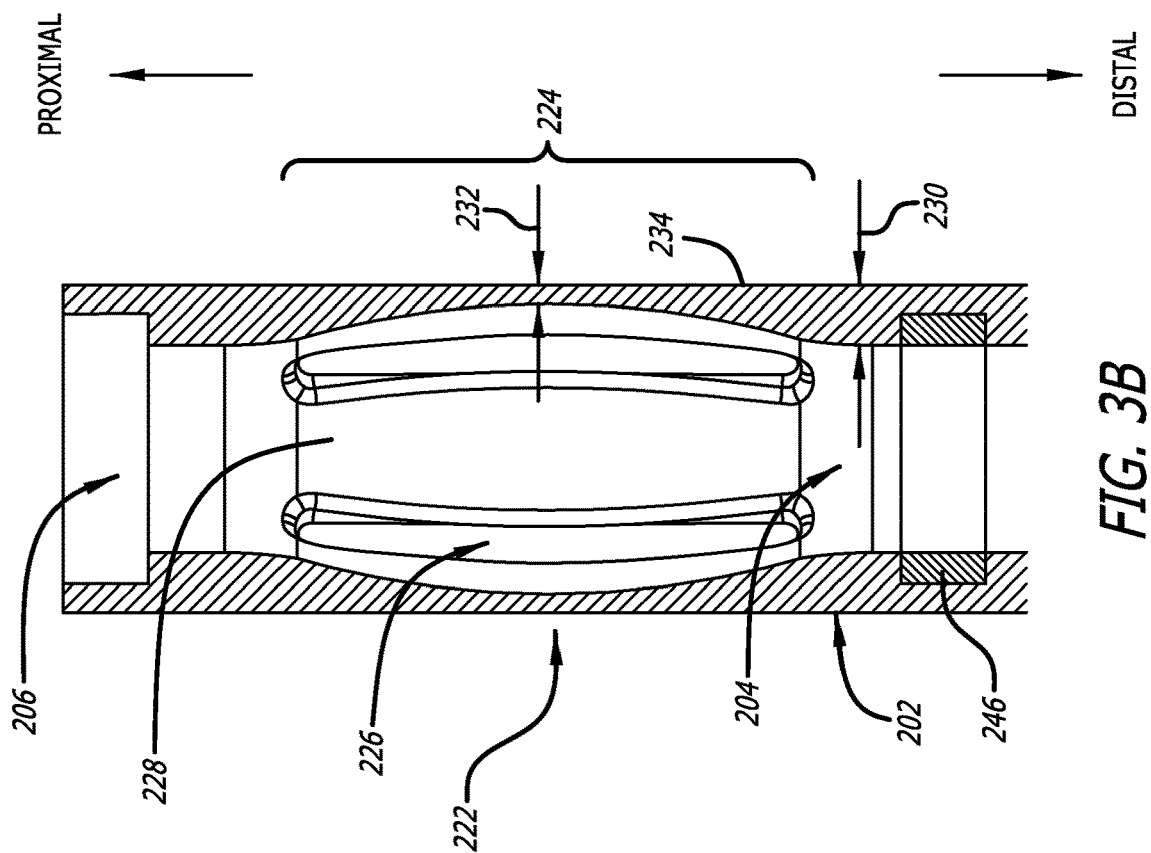
FIG. 3B illustrates a cross-sectional view of a collapsible section of the indwelling catheter including some components of the guidewire anchoring mechanism, in accordance with some embodiments.
Figure 3A:
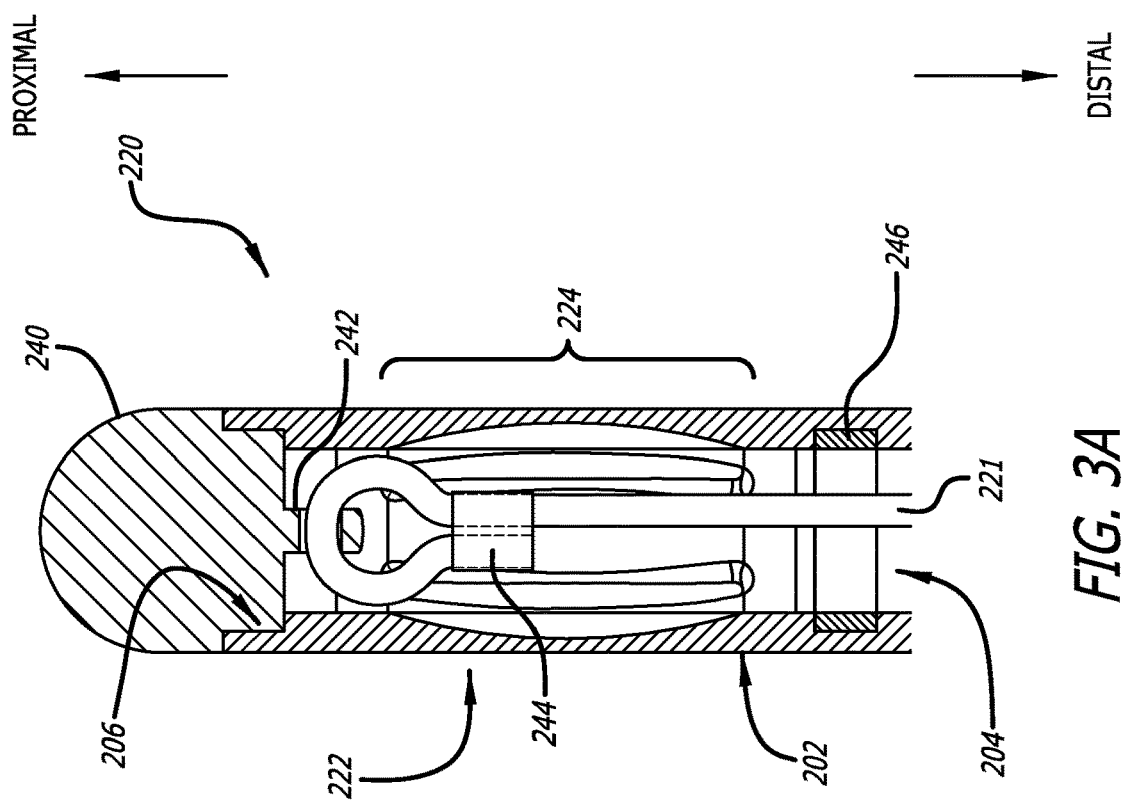
FIG. 3A illustrates a cross sectional view of a proximal end of the indwelling catheter including a proximal portion of the guidewire anchoring mechanism, in accordance with some embodiments.

FIG. 3A illustrates a cross sectional view of the proximal end of the catheter 200 including the proximal portion of the guidewire anchoring mechanism 220, in accordance with some embodiments. In some embodiments, the proximal portion of the guidewire anchoring mechanism 220 may include the top cap 240 having a top cap ring 242, a crimp bead 244, a bottom ring 246, the collapsible section 224 including the bladder opening 222 and a proximal end of the guidewire 221. The top cap 240 may be coupled to the proximal opening 206 of the catheter tube 202 through a twist fit, a snap fit, an interference fit or the like. The top cap 240 includes a top cap ring 242, distally extending from the top cap 240 into the catheter tube lumen 204. A proximal end of the guidewire 221 may be coupled to the top cap ring 242 by threading the proximal end of the guidewire 221 through the top cap ring 242 and coupling the proximal end of the guidewire 221 to the guidewire 221. The proximal end of the guidewire 221 may be coupled back to the guidewire 221 by the crimp bead 244, providing an anchor point for the guidewire 221. Advantageously, the proximal end of the guidewire 221 being coupled to guidewire 221 by the crimp bead 244 allows mechanical movement in the distal portion of the guidewire anchoring mechanism 220 to translate to mechanical movement in the proximal portion of the guidewire anchoring mechanism 220. The bottom ring 246 may reside within the catheter tube lumen 204, distal the bladder opening 222 to help stabilize the guidewire 221 within the catheter tube lumen 204.

FIG. 3B illustrates a cross-sectional view of a collapsible section 224 of the indwelling catheter 200 including some components of the guidewire anchoring mechanism 220, in accordance with some embodiments. In some embodiments, the catheter tube 202 may include a first wall thickness 230, wherein the first wall thickness 230 is the distance between an external surface 234 of the catheter tube 202 and the catheter tube lumen 204. In some embodiments, the catheter tube 202 may have the first wall thickness 230 along the entire catheter tube 202 except for the collapsible section 224. In some embodiments, the collapsible section 224 may include a second wall thickness 232 that is less than the first wall thickness 230. The difference between the first wall thickness 230 and the second wall thickness 232 may configure the collapsible section 224 of the catheter tube 202 to collapse distally under a distal pulling force from the guidewire 221, that will be described in more detail herein. In some embodiments, the collapsible section 224 may include the bladder opening 222 comprised of a plurality of vertical slits 226. The plurality of vertical slits 226 define a plurality of flexible bands 228. The plurality of flexible bands 228 may be compressed, or collapsed, to horizontally expand the flexible bands 228, that will be described in more detail herein. The plurality of vertical slits 226 may be configured to provide fluid communication between the catheter tube lumen 204 and the external surface 234, allowing fluid from within the bladder to enter into the catheter tube lumen 204.

FIG. 4A illustrates a cross sectional view of the distal portion of the guidewire anchoring mechanism 220, in accordance with some embodiments. In some embodiments, the catheter tube 202 may be coupled to the holder 250, as illustrated in FIG. 4A. The holder 250 includes a holder lumen 252. In some embodiments, the catheter tube 202 may include a guidewire opening 210 configured to allow the guidewire 221 to exit the catheter tube lumen 204 and enter the holder lumen 252. In some embodiments, the holder cap 256 may be coupled to the holder 250 in a snap fit, an interference fit, a twist fit or the like. The distal end of the guidewire 221 may extend through the holder lumen 252 and the holder cap 256. In some embodiments, the holder lumen 252 may be separated from the holder cap 256 by a septum 254. The septum 254 may be configured to provide a fluid tight seal, preventing fluid traveling through the catheter tube lumen 204 to the holder cap 256 but may be configured to allow the guidewire 221 to pass through the septum 254 to the holder cap 256. In some embodiments, the holder cap 256 includes a holder cap channel 258 having a holder cap channel diameter 259. In some embodiments, the holder cap channel 258 may be in communication with one or more guidewire channels 260. The one or more guidewire channels 260 may be configured to receive therethrough the distal end of the guidewire 221, allowing a user to provide a pulling force on the distal end of the guidewire 221. The distal end of the guidewire 221 may include a guidewire bump 280, the guidewire bump 280 being a protrusion extending from the guidewire 221. The guidewire bump 280 may include a guidewire bump diameter 282, that is less than the holder cap channel diameter 259, allowing the guidewire bump 280 to move within the holder cap lumen 258. In some embodiments, the guidewire bump 280 may be configured to fit through one or more of the guidewire channels 260, allowing the guidewire bump 280 to move from the holder cap lumen 258 to outside the holder cap 256.

FIG. 4B illustrates a perspective view of the distal portion of the guidewire anchoring mechanism 220, in accordance with some embodiments. In some embodiments, the holder cap 256 includes a first guidewire channel 260 or a second guidewire channel 262, each in communication with the holder cap channel 258. In some embodiments, the distal end of the guidewire 221, but not the guidewire bump 280, may fit through the first guidewire channel 260 and the second guidewire channel 262, whereas the guidewire bump 280 may only fit through the second guidewire channel 262. As illustrated in FIG. 4B, in some embodiments, the first guidewire channel 260 may be connected to the second guidewire channel 262, allowing the user to slide the distal end of the guidewire 221 between the first guidewire channel 260 and the second guidewire channel 262. The distal end of the guidewire 221 may be pulled until the guidewire bump 280 reaches the first guidewire channel 260, then may be moved to the second guidewire channel 262 and pulled through the second guidewire channel 262 until the guidewire bump 280 is through the second guidewire channel 262. The distal end of the guidewire 221 may then be moved back to the first guidewire channel 260. In an embodiment, the holder cap 256 may be configured to rotate annularly, allowing the user to pull the distal end of the guidewire 221 and rotate the holder cap 256 until the second guidewire channel 262 lines up with the guidewire bump 280. The user may then rotate the holder cap 256 until the first guidewire channel 260 lines up with the guidewire 221.

Figure 5C:
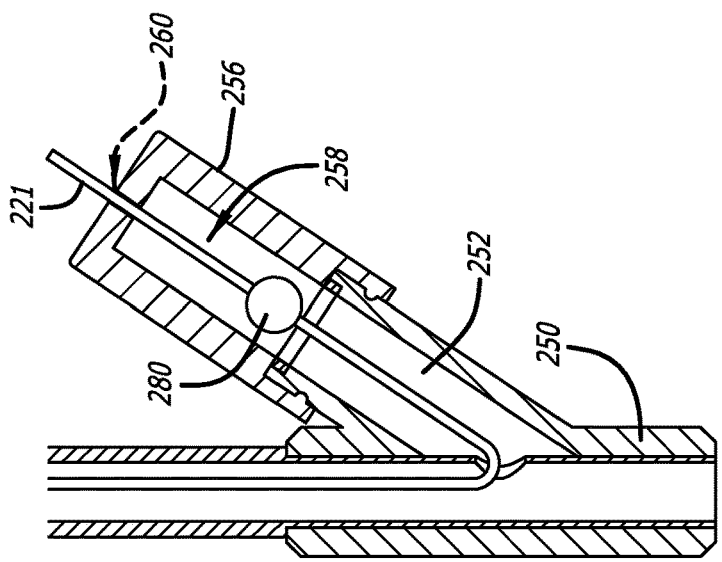
FIG. 5C illustrates a cross sectional view of the distal portion of the guidewire anchoring mechanism in the insertion state, in accordance with some embodiments.
Figure 5B:
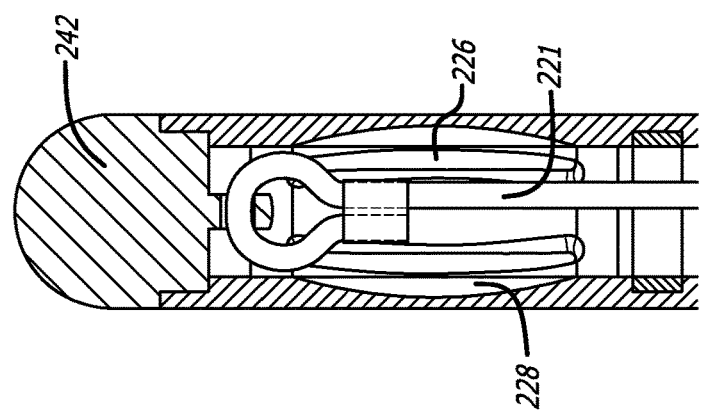
FIG. 5B illustrates a cross sectional view of the proximal end of the indwelling catheter including a proximal portion of the guidewire anchoring mechanism in the insertion state, in accordance with some embodiments.
Figure 5A:
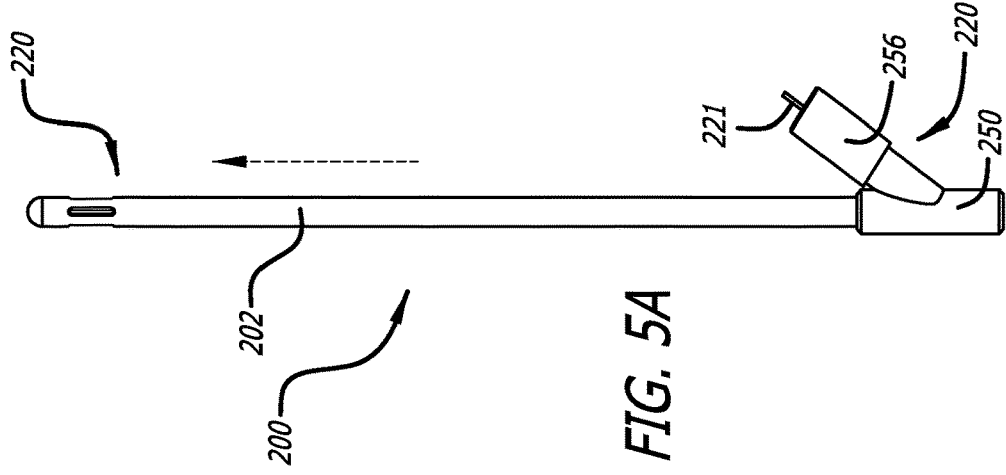
FIG. 5A illustrates a side perspective view of the indwelling catheter including the guidewire anchoring mechanism in the insertion state, in accordance with some embodiments.

FIG. 5A illustrates a side perspective view of the indwelling urinary catheter 200 in an insertion state, in accordance with some embodiments. In some embodiments, the indwelling urinary catheter 200 may have the insertion state and an anchored state. The guidewire anchoring mechanism 220 may facilitate the transition between the insertion state, configured to allow the catheter 200 to be inserted into the bladder, and the anchored state, configured to anchor the catheter 200 within the bladder. Advantageously, the guidewire anchoring mechanism 220 can transition from the anchored state to the insertion state to facilitate removal of the catheter 200 from the bladder. In some embodiments, the catheter 200 may be biased towards the insertion state. In the insertion state, as illustrated in FIG. 5B, the proximal portion of the guidewire anchoring mechanism 220 includes the plurality of flexible bands 228 being in a vertical position. As illustrated in FIG. 5C, the distal portion of the guidewire anchoring mechanism 220 includes the guidewire bump 280 within the holder cap channel 258 and the distal end of the guidewire 221 extending through the first guidewire channel 260.

Figure 5F:
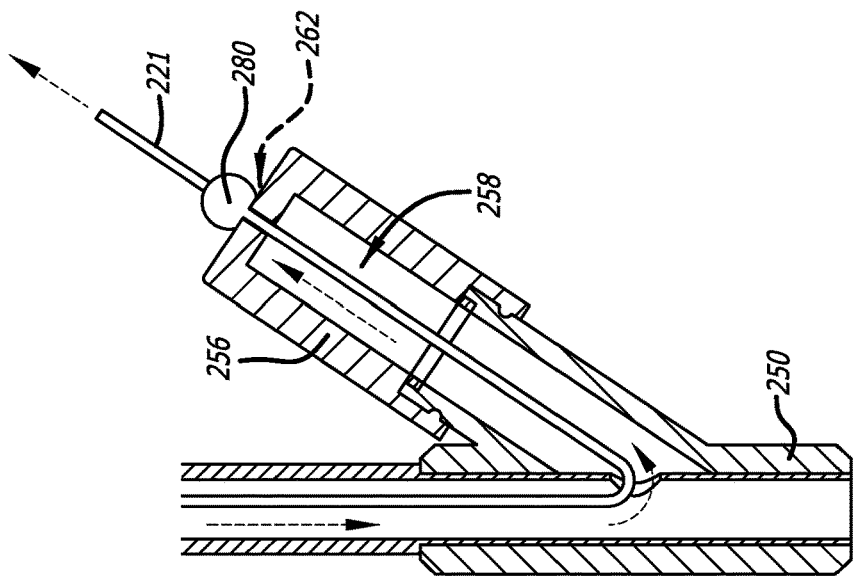
FIG. 5F illustrates a cross sectional view of the distal portion of the guidewire anchoring mechanism in the activated state, in accordance with some embodiments.
Figure 5E:
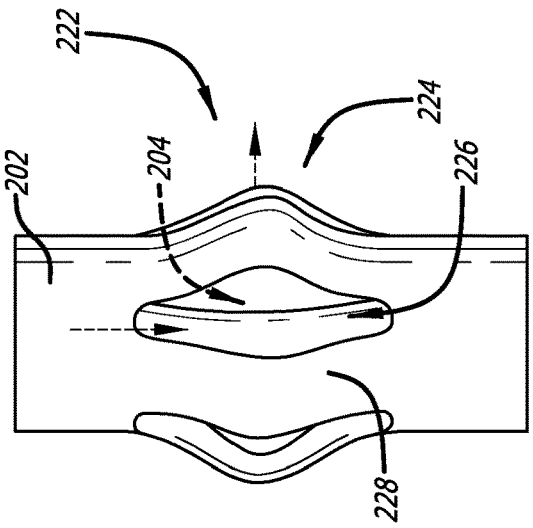
FIG. 5E illustrate a perspective view of a collapsible section of the guidewire anchoring mechanism in the activated state, in accordance with some embodiments.
Figure 5D:
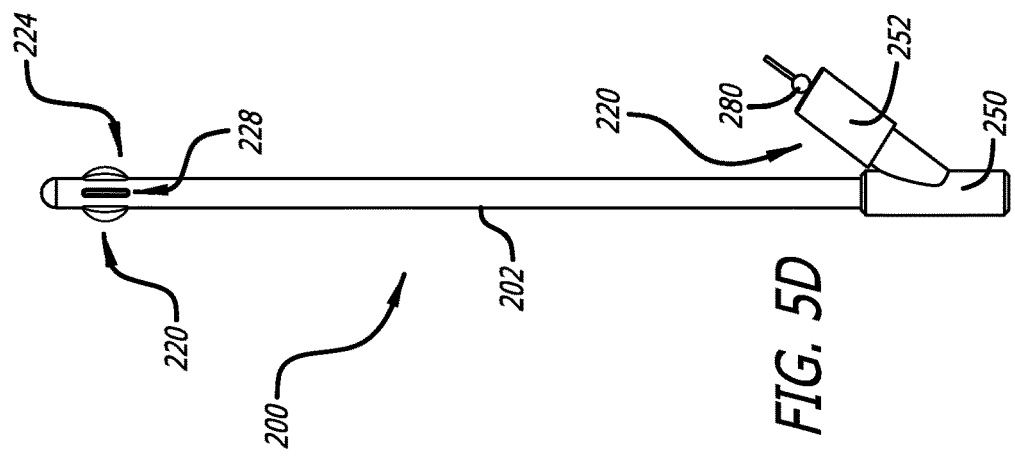
FIG. 5D illustrates a side perspective view of the indwelling catheter including the guidewire anchoring mechanism in an activated state, in accordance with some embodiments.

FIG. 5D illustrates a side perspective view of the indwelling urinary catheter 200 in the anchored state, in accordance with some embodiments. In the anchored state, the collapsible portion 224 of the proximal portion of the guidewire anchoring mechanism 220 has extended horizontally, to anchor the catheter 200 within the bladder. The distal end of the guidewire 221 has been pulled, allowing the proximal end of the guidewire 221 to collapse the collapsible portion 224 due to the difference in the first wall thickness and the second wall thickness. As illustrated in FIG. 5E, the plurality of flexible bands 228 have been compressed by the pulling force of the guidewire 221, allowing the plurality of flexible bands 228 to expand horizontally, anchoring the catheter 200 in the bladder. The plurality of flexible bands 228 expanding horizontally enlarges the plurality of vertical slits 226 comprising the bladder opening 222, allowing fluid to enter through the plurality of vertical slits 226 into the catheter tube lumen 204. As illustrated in FIG. 5F, the pulling force on the distal end of the guidewire 221, pulls the guidewire bump 280 through the holder cap lumen 258 and out of the holder cap 256 through the second guidewire channel 262. In some embodiments, the user may pull the guidewire bump 280 through the second guidewire channel 262 and then transition the distal end of the guidewire 221 to the first guidewire channel 260 to maintain the catheter 200 in the anchored state.

Figure 6:
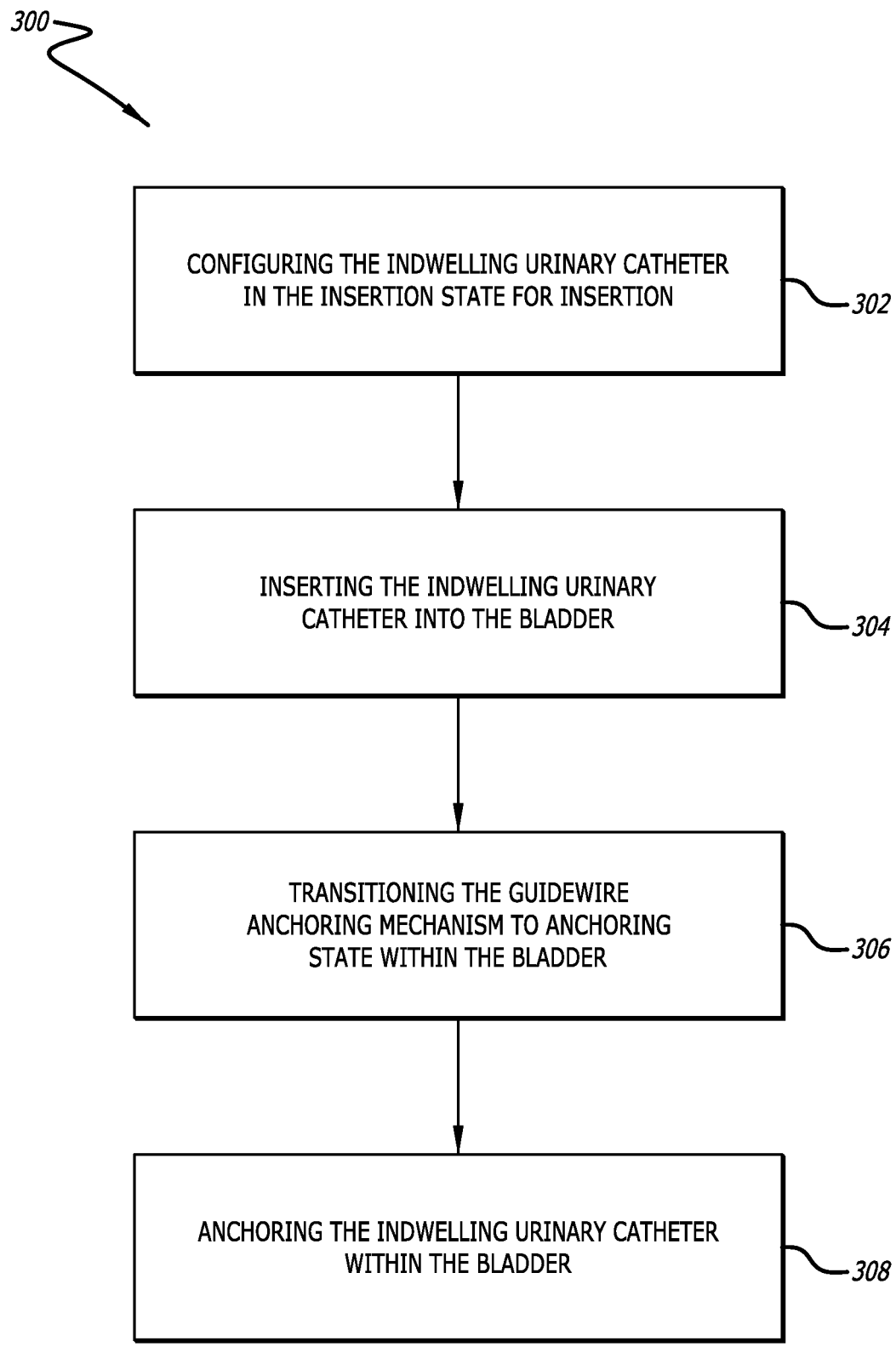
FIG. 6 illustrates a flow chart of an exemplary method of placing an indwelling urinary catheter, in accordance with some embodiments.

FIG. 6 illustrates a flow chart of an exemplary method 300 of placing and anchoring an indwelling urinary catheter 200, in accordance with some embodiments. In some embodiments, the method 300 includes configuring the indwelling urinary catheter 200 for insertion into the bladder (block 302). In some embodiments, configuring includes placing the guidewire anchoring mechanism 220 of the indwelling urinary catheter 200 in the insertion state. In some embodiments, placing the guidewire anchoring mechanism 220 in the insertion state includes placing the collapsible section 224 of the guidewire anchoring mechanism 220 in the insertion state. In some embodiments, the insertion state includes the plurality of flexible bands 228 in a vertical orientation and the distal end of the guidewire 221 extending through the first guidewire channel 260 of the holder cap 256.

In some embodiments, the method 300 includes inserting the indwelling urinary catheter 200 including the guidewire anchoring mechanism 220 in the insertion state, into the bladder (block 304). In some embodiments, the method 300 includes transitioning the guidewire anchoring mechanism 220 to an anchored state (block 306). In some embodiments, transitioning the guidewire anchoring mechanism 220 to an anchored state includes transitioning the collapsible section 224 to the anchored state. In some embodiments, in the anchored state, the collapsible section 224 includes the plurality of flexible bands 228 being horizontally extended and the guidewire bump 280 of the distal end of the guidewire 221 is pulled through the second guidewire channel 262 of the holder cap 256. In some embodiments, transitioning the guidewire anchoring mechanism 220 to the anchored state includes a pulling force on the distal end of the guidewire 221 transitioning the collapsible section 224 to the anchored state. In some embodiments, the pulling force on the distal end of the guidewire 221 transitioning the collapsible section 224 includes the proximal end of the guidewire 221 threaded through the top cap ring 242 of the top cap 240 coupled to the proximal opening 206 of the catheter tube 202. In some embodiments, the pulling force may be configured to collapse the collapsible section 224 to horizontally extend the plurality of flexible bands 228.

The method 300 further includes anchoring the indwelling urinary catheter 200 within the bladder (block 308). In some embodiments, anchoring includes transitioning the distal end of the guidewire 221 to the first guidewire channel 260 to maintain the anchored state within the bladder.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An indwelling urinary catheter, comprising:
a catheter tube having a proximal opening, a distal opening, and a catheter tube lumen therethrough, the catheter tube having a first wall thickness; and
a guidewire anchoring mechanism configured to transition between an insertion state and an anchored state, comprising:
  a proximal portion including a top cap and a collapsible section of the catheter tube having a second wall thickness less than the first wall thickness;
  a distal portion including a holder cap coupled to a holder, wherein the holder is coupled to the catheter tube, the distal portion being in communication with the proximal portion; and
  a guidewire coupled to the proximal portion and extending through the holder cap and the catheter tube lumen to the distal portion, a distal end of the guidewire including a guidewire bump having a cross section greater than the guidewire, wherein the holder cap includes:
    a first guidewire channel sized to prevent passage of the guidewire bump therethrough; and
    a second guidewire channel sized to allow passage of the guidewire bump therethrough,
  wherein:
    the catheter tube further includes a guidewire opening extending through a side wall of the catheter tube, the guidewire exiting the catheter tube lumen through the guidewire opening, and
    the indwelling urinary catheter is configured such that fluid is:
      allowed to exit the indwelling urinary catheter via the distal opening, and
      prevented from exiting the indwelling urinary catheter via the guidewire opening.

2. The indwelling urinary catheter according to claim 1, wherein the collapsible section includes a plurality of vertical slits that define a plurality of flexible bands, the plurality of flexible bands being configured to exist in a vertical position or be horizontally extended.

3. The indwelling urinary catheter according to claim 2, wherein the top cap is coupled to the proximal opening of the catheter tube, and a top cap ring distally extends from the top cap into the catheter tube lumen.

4. The indwelling urinary catheter according to claim 3, wherein a proximal end of the guidewire is threaded through the top cap ring and coupled to the guidewire.

5. The indwelling urinary catheter according to claim 4, wherein the proximal end of the guidewire is threaded through the top cap ring and coupled to the guidewire by a crimp bead.

6. The indwelling urinary catheter according to claim 1, wherein the distal portion includes the holder having a holder lumen configured to receive the distal end of the guidewire therethrough, and the holder cap having a holder cap channel in communication with each of the first guidewire channel and the second guidewire channel, each of the first guidewire channel and the second guidewire channel configured to receive therethrough the guidewire.

7. The indwelling urinary catheter according to claim 6, wherein the holder lumen is separated from the holder cap channel by a septum configured to provide a fluid tight seal preventing fluid traveling through the catheter tube lumen to reach the holder cap.

8. The indwelling urinary catheter according to claim 1, wherein the guidewire opening is configured to allow the guidewire to be threaded from the catheter tube lumen to the holder.

9. The indwelling urinary catheter according to claim 1, wherein the second guidewire channel is configured to receive therethrough the guidewire bump, and the first guidewire channel is configured to receive therethrough only the guidewire.

10. The indwelling urinary catheter according to claim 2, wherein the insertion state includes the distal end of the guidewire extending through the first guidewire channel and the plurality of flexible bands being in a vertical position.

11. The indwelling urinary catheter according to claim 10, wherein the anchored state includes:
the plurality of flexible bands being horizontally extended;
the guidewire bump being distally displaced through the second guidewire channel; and
the guidewire bump being captured in the first guidewire channel.

12. The indwelling urinary catheter according to claim 11, wherein a pulling force on the distal end of the guidewire transitions the guidewire anchoring mechanism from the insertion state to the anchored state.

13. The indwelling urinary catheter according to claim 12, wherein the indwelling urinary catheter is biased to the insertion state.

14. A method of anchoring an indwelling urinary catheter in a bladder, comprising:
providing the indwelling urinary catheter configured for insertion into the bladder, the indwelling urinary catheter having a guidewire anchoring mechanism configured in an insertion state;
inserting the indwelling urinary catheter into the bladder;
transitioning the guidewire anchoring mechanism from the insertion state to an anchored state to anchor the indwelling urinary catheter within the bladder,
wherein:
  the indwelling urinary catheter includes a catheter tube having:
    a proximal opening;
    a distal opening;
    a catheter tube lumen therethrough; and
    a guidewire opening extending through a side wall of the catheter tube, and the indwelling catheter is configured such that fluid is:
      allowed to exit the indwelling urinary catheter via the distal opening, and
      prevented from exiting the indwelling urinary catheter via the guidewire opening, and
  wherein the guidewire anchoring mechanism includes:
    a guidewire extending through the guidewire opening, the guidewire including a guidewire bump at a distal end of the guidewire, the guidewire bump having greater cross section greater than the guidewire, and
    a holder cap coupled with the catheter tube, the holder cap including:

a first guidewire channel sized to prevent passage of the guidewire bump therethrough; and a second guidewire channel sized to allow passage of the guidewire bump therethrough.

15. The method according to claim 14, wherein:

the catheter tube includes a first wall thickness, and the guidewire anchoring mechanism further includes:

a collapsible section of the catheter tube having a second wall thickness less than the first wall thickness and a plurality of vertical slits that define a plurality of flexible bands, the plurality of flexible bands disposed in a vertical orientation when the guidewire anchoring mechanism is disposed in the insertion state.

16. The method according to claim 15, wherein transitioning the guidewire anchoring mechanism to the anchored state includes:

transitioning the collapsible section to a collapsed state, such that the plurality of flexible bands are horizontally extended; and distally displacing the guidewire bump through the second guidewire channel of the holder cap.

17. The method according to claim 16, wherein the guidewire anchoring mechanism is transitioned to the anchored state by applying a pulling force on the distal end of the guidewire in order to transition the collapsible section to the collapsed state.

18. The method according to claim 17, wherein:

the indwelling urinary catheter further includes a top cap coupled to the proximal opening of the catheter tube and the guidewire via a top cap ring of the top cap, and transitioning the guidewire anchoring mechanism to the anchored state includes distally displacing the top cap to transition the collapsible section to the collapsed state.

19. The method according to claim 18, wherein anchoring the indwelling urinary catheter within the bladder includes maintaining the guidewire anchoring mechanism in the anchored state within the bladder by moving the distal end of the guidewire from the second guidewire channel to the first guidewire channel.

\* \* \* \* \*